(12) United States Patent
Iwanami et al.

(10) Patent No.: US 10,870,143 B2
(45) Date of Patent: Dec. 22, 2020

(54) CONNECTION STRUCTURE AND CONNECTION METHOD

(71) Applicant: OLYMPUS CORPORATION, Hachioji (JP)

(72) Inventors: Takayoshi Iwanami, Hachioji (JP); Yuta Muyari, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 159 days.

(21) Appl. No.: 15/984,815

(22) Filed: May 21, 2018

(65) Prior Publication Data

US 2018/0263650 A1    Sep. 20, 2018

Related U.S. Application Data

(63) Continuation of application No. PCT/JP2016/083666, filed on Nov. 14, 2016.

(30) Foreign Application Priority Data

Nov. 25, 2015   (JP) .................. 2015-229596

(51) Int. Cl.
*B21F 15/06*    (2006.01)
*A61B 17/00*    (2006.01)

(52) U.S. Cl.
CPC .... *B21F 15/06* (2013.01); *A61B 2017/00526* (2013.01)

(58) Field of Classification Search
CPC ..... H01R 4/20; H01R 11/07; A61B 17/32056; Y10T 29/49933
See application file for complete search history.

(56) References Cited

U.S. PATENT DOCUMENTS 2,109,517 A * 3/1938 Xenis ................. H01R 4/48
                                                    403/20
2,109,837 A * 3/1938 Davis ................. H01R 4/20
                                                    29/517

(Continued)

FOREIGN PATENT DOCUMENTS

CN    101416863 A    4/2009
JP      3073285 U   11/2000

(Continued)

OTHER PUBLICATIONS

Japanese Office Action dated Jul. 2, 2019 (and English translation thereof) issued in counterpart Japanese Application No. 2015-229596.

(Continued)

*Primary Examiner* — Jason L Vaughan
(74) *Attorney, Agent, or Firm* — Holtz, Holtz & Volek PC

(57) ABSTRACT

A connection structure includes: a first wire; a second wire having a diameter smaller than a diameter of the first wire; a connection member configured to connect the first wire and the second wire, wherein a distal end portion of the first wire is inserted from an opening portion at one end of the connection member to be crimped, and a proximal end portion of the second wire is inserted from an opening portion at another end of the connection member to be crimped, the opening portion at the other end having a diameter smaller than a diameter of the opening portion at the one end.

7 Claims, 10 Drawing Sheets

(56) References Cited

U.S. PATENT DOCUMENTS

| | | | | |
|---|---|---|---|---|
| 3,006,983 | A | * | 10/1961 | McDurmont ............ H01R 4/20 174/94 R |
| 3,211,829 | A | * | 10/1965 | Brautigam ............. H01B 17/12 174/79 |
| 3,422,529 | A | * | 1/1969 | Nuding .................... H01R 4/20 29/599 |
| 3,842,497 | A | * | 10/1974 | Kehl ........................ H01R 4/20 29/862 |
| 6,310,292 | B1 | * | 10/2001 | Osborn ................... H01R 4/20 174/84 C |
| 6,602,262 | B2 | * | 8/2003 | Griego ............. A61B 17/32056 606/110 |
| 6,658,735 | B2 | * | 12/2003 | Ito ........................... H01R 4/183 174/84 C |
| 7,256,348 | B1 | * | 8/2007 | Endacott ................ H01R 4/183 174/84 C |
| 7,951,073 | B2 | * | 5/2011 | Freed ............... A61B 17/32056 600/159 |
| 8,186,035 | B2 | | 5/2012 | Kaneko et al. |
| 8,216,247 | B2 | | 7/2012 | Kaneko et al. |
| 8,851,939 | B2 | * | 10/2014 | Bazenas ................. F16F 1/045 439/840 |
| 9,799,969 | B2 | * | 10/2017 | Lee .......................... H01R 4/60 |
| 2009/0112225 | A1 | | 4/2009 | Kaneko et al. |
| 2017/0273737 | A1 | | 9/2017 | Iwanami et al. |

FOREIGN PATENT DOCUMENTS

| | | |
|---|---|---|
| JP | 2001218771 A | 8/2001 |
| JP | 2003311355 A | 11/2003 |
| JP | 2009101153 A | 5/2009 |
| JP | 2012157378 A | 8/2012 |
| WO | 2016103820 A1 | 6/2016 |

OTHER PUBLICATIONS

International Search Report (ISR) dated Jan. 10, 2017 issued in International Application No. PCT/JP2016/083666.

Written Opinion dated Jan. 10, 2017 issued in International Application No. PCT/JP2016/083666.

Chinese Office Action (and English language translation thereof) dated Apr. 14, 2020 issued in Chinese Application No. 201680067224.1.

* cited by examiner

CONNECTION STRUCTURE AND CONNECTION METHOD

CROSS-REFERENCE TO RELATED APPLICATION

This application is a continuation of PCT International Application No. PCT/JP2016/083666 filed on Nov. 14, 2016 which claims the benefit of priority from Japanese Patent Application No. 2015-229596, filed on Nov. 25, 2015, the entire contents of which are incorporated herein by reference.

BACKGROUND

The present disclosure relates to a connection structure and a connection method.

As a treatment instrument used in a medical endoscope, a treatment instrument which is inserted into a lumen from a distal end portion of an endoscope insertion portion and resects a body tissue such as a polyp by tightening the body tissue by a snare which is a loop-shaped wire is known (for example, see JP 2001-218771 A). In the treatment instrument, it is common to use a high-frequency snare (hot snare) that cauterizes and resects a tightened body tissue by applying a high-frequency current to the snare.

In the high-frequency snare, since the resection is performed while thermally coagulating the body tissue (stop bleeding), intraoperative bleeding may be suppressed, but large bleeding is accompanied after surgery in some cases. Further, in the high-frequency snare, since a high-frequency power source needs to be prepared and a counter electrode plate needs to be attached to a patient, preparations before surgery are complicated. Additionally, in the case of the high-frequency snare, it is necessary to pay attention to burns or the like of the patients and surgeons during surgery.

Under such circumstances, a technique which is called a cold snare and resects a body tissue only by tightening a wire without flowing a high-frequency current to the snare has been widely distributed in recent years. The resection of the body tissue by the cold snare is accompanied by bleeding because this technique cannot be expected to stop bleeding due to thermal coagulation like a high-frequency snare. However, since its effect is limited to the resected part, invasiveness is low. Further, the cold snare does not need complicated preparations before surgery like the case of the high-frequency snare.

On the other hand, in the case of the cold snare, it is essential to use a sharp snare in order to minimize bleeding in the body and to resect the body tissue. In order to form the sharp snare, it is most effective to form the snare by using a wire having a small diameter. Accordingly, since the snare may easily protrude into the body tissue by cutting when the body tissue is tightened, it is possible to resect the body tissue with small bleeding.

SUMMARY

A connection structure according to one aspect of the present disclosure includes: a first wire; a second wire having a diameter smaller than a diameter of the first wire; a connection member configured to connect the first wire and the second wire, wherein a distal end portion of the first wire is inserted from an opening portion at one end of the connection member to be crimped, and a proximal end portion of the second wire is inserted from an opening portion at another end of the connection member to be crimped, the opening portion at the other end having a diameter smaller than a diameter of the opening portion at the one end.

A connection method according to another aspect of the present disclosure connects a first wire to a second wire having a diameter smaller than a diameter of the first wire by using a connection member, and includes: inserting a distal end portion of the first wire from an opening portion at one end of the connection member to be crimped; reducing a diameter of a hollow portion including an opening portion at another end of the connection member; and inserting a proximal end portion of the second wire from the opening portion at the other end to be crimped.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
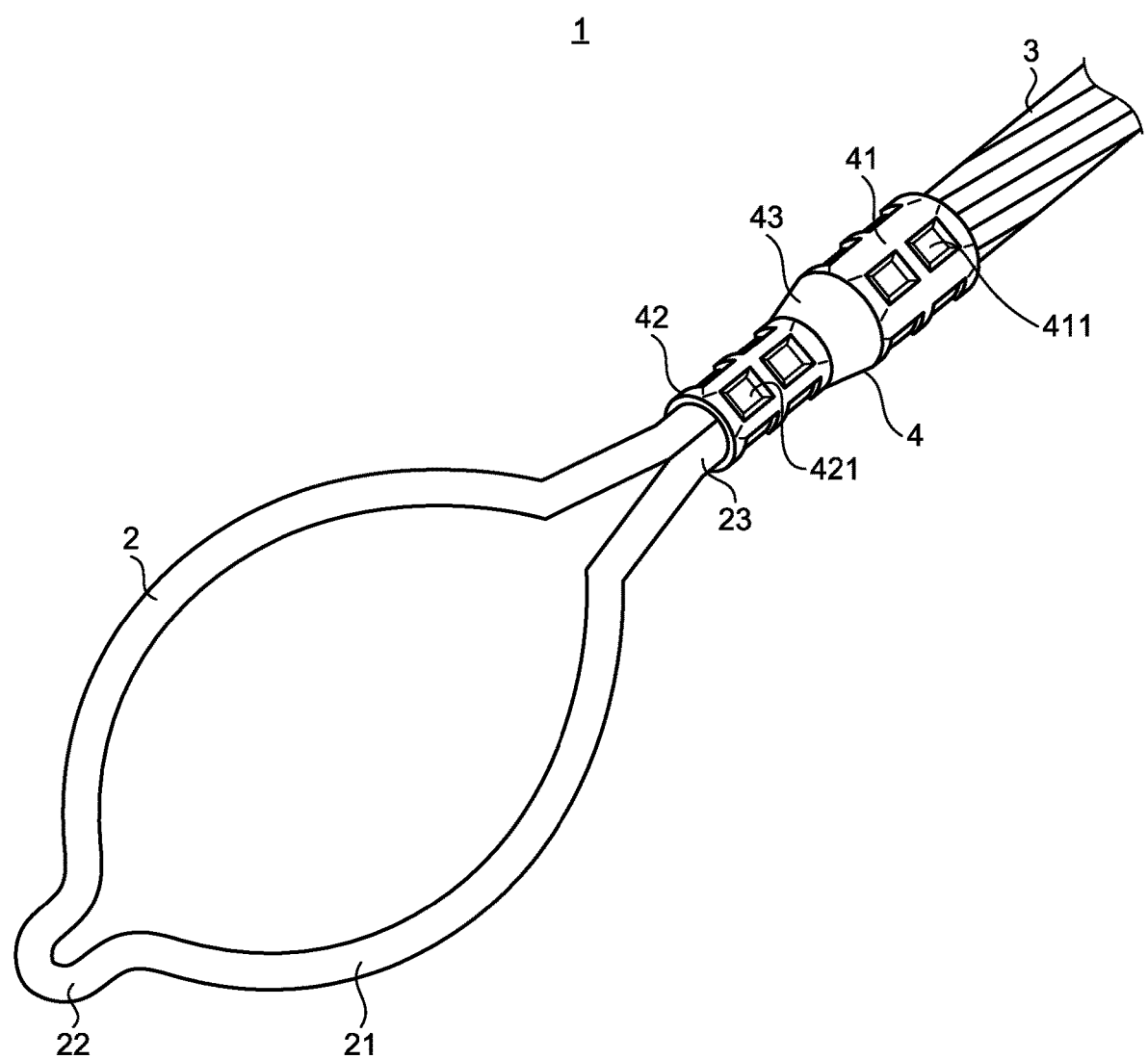
FIG. 1 is a diagram illustrating an outline of a connection structure including a connection structure according to an embodiment.

Hereinafter, a mode for carrying out the present disclosure (hereinafter, referred to as an "embodiment") will be described in detail on the basis of the accompanying drawings. Incidentally, the drawings are schematic and the relationships or ratios of the dimensions of the components are different from the reality. Further, also in the drawings, portions in which the relationships or ratios of dimensions are different from each other are included.

FIG. 1 is a diagram illustrating an outline of a connection structure including a connection structure according to an embodiment. A connection structure 1 illustrated in FIG. 1 includes a loop-shaped snare 2 (a second wire), an operation wire 3 (a first wire) located at a proximal end side of the snare 2, and a connection member 4 connecting the snare 2 and the operation wire 3 to each other.

The snare 2 is formed by using a stranded wire (metal wire) made of a metal element wire of stainless steel SUS304 and includes a loop portion 21 which has a substantially oval shape, a distal end portion 22 which is located at an end portion opposite to an end portion bonded to the connection member 4 and corresponding to one end portion of the loop portion 21 in the long diameter direction and in which a stranded wire is folded in a U-shape, and a proximal end portion 23 in which both end portions of the wires are arranged side by side.

Figure 2:
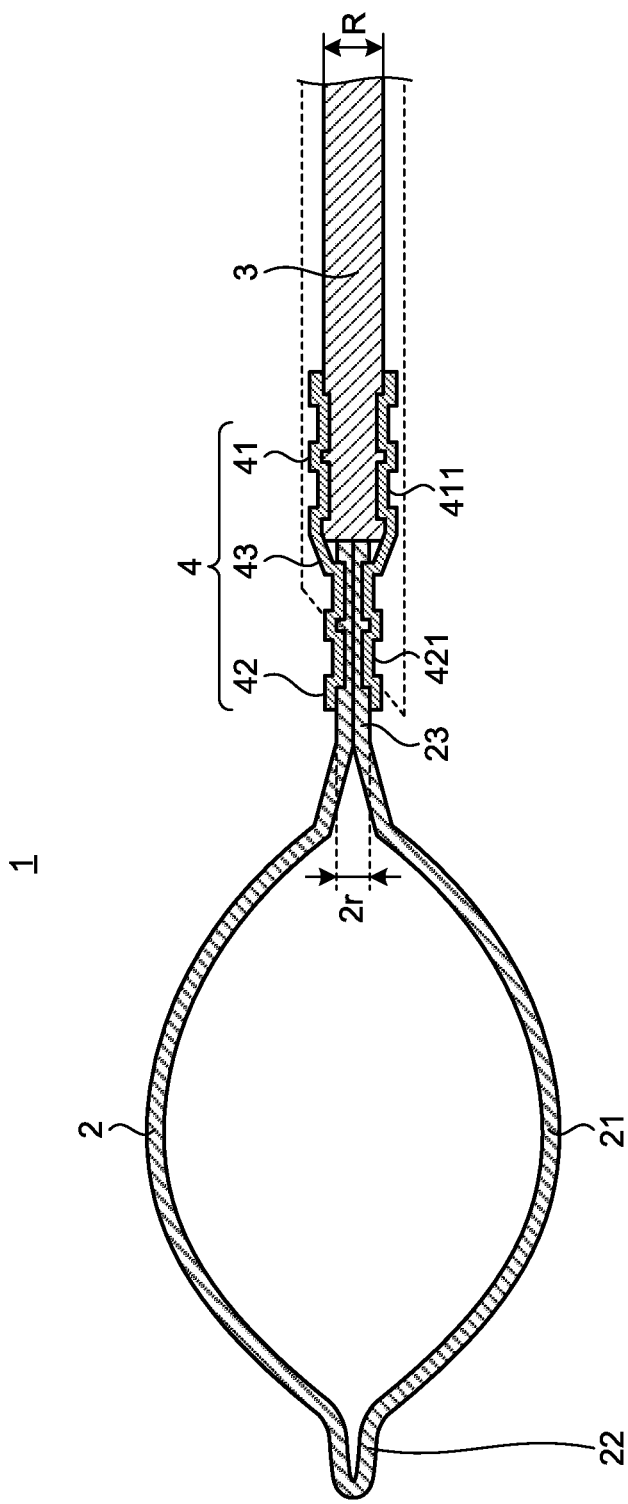
FIG. 2 is a cross-sectional view cut along a plane passing through a loop portion of a snare.

FIG. 2 is a cross-sectional view cut along a plane passing through the loop portion 21 of the snare 2. When the outer diameter of the wire constituting the snare 2 is indicated by r and the outer diameter of the operation wire 3 is indicated by R, the total wire diameter 2r in a state where both ends of the wires are arranged at the proximal end portion 23 is smaller than the diameter R of the operation wire 3. It is more preferable that the diameter r of the wire is equal or smaller than ⅓ of the diameter R of the operation wire 3 (0<r≤R/3).

Similarly to the snare 2, the operation wire 3 is formed by using, for example, stainless steel SUS304. It is desirable that the operation wire 3 has a force transferability capable of surely deploying the snare 2 from a flexible sheath (indicated by a broken line in FIG. 2) provided in the treatment instrument under any circumstance. Specifically, it is desirable that the operation wire 3 has force transferability capable of surely deploying the snare 2 from the distal end of the insertion portion even in a state unfavorable for deployment of the snare 2 as in the state where the snare 2 is located in the curved portion of the insertion portion of the endoscope, for example.

The connection member 4 includes a wire connection portion 41 which is connected to the operation wire 3, a snare connection portion 42 which has a diameter smaller than that of the wire connection portion 41 and is connected to the snare 2, and an intermediate portion 43 which is located between the wire connection portion 41 and the snare connection portion 42 and is formed in a tapered shape. For the wire connection portion 41, the distal end portion of the operation wire 3 is inserted from an opening portion of one end side of the connection member 4 to be crimped. For the snare connection portion 42, the proximal end portion 23 of the snare 2 is inserted from an opening portion at the other end side of the connection member 4 to be crimped, the opening portion having a diameter smaller than that of an opening portion at the insertion side of the operation wire 3.

The connection member 4 is made of, for example, a pipe material of stainless steel SUS304. The inner diameter dimension of the connection member 4 is set so that a gap with respect to the outer diameter dimension of the operation wire 3 decreases as small as possible. In this setting, it is desirable to set the size of the gap that may achieve both of the bonding strength and the assembling workability in consideration of the dimensional tolerance of the operation wire 3 and the connection member 4.

Figure 3:
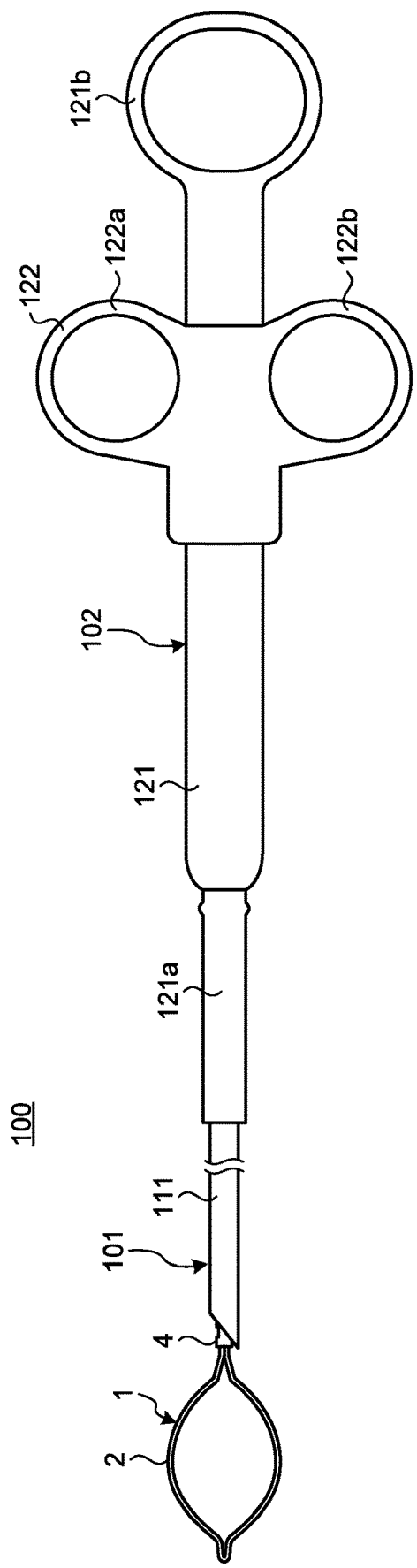
FIG. 3 is a plan view illustrating an external configuration of a treatment instrument for an endoscope including the connection structure according to the embodiment.

FIG. 3 is a plan view illustrating an external configuration of the treatment instrument for the endoscope having the connection structure 1. A treatment instrument 100 illustrated in FIG. 3 includes an insertion portion 101 which is insertable through a channel of the treatment instrument of the endoscope and an operating unit 102 which is provided at the proximal end side of the insertion portion 101 in addition to the snare 2, the operation wire 3, and the connection member 4 constituting the connection structure 1.

The insertion portion 101 includes a flexible sheath 111 which accommodates the snare 2, the operation wire 3, and the connection member 4 to be movable forward and backward. It is desirable that the flexible sheath 111 is a material having a small friction with respect to a material forming the connection structure 1 and having rigidity with excellent force transferability and is formed by using, for example, fluororesin such as Teflon (registered trademark) resin or polyethylene. The distal end of the flexible sheath 111 is inclined by 45° with respect to the axial direction. Accordingly, it is possible to prevent the flexible sheath 111 from collapsing when tightening a body tissue by the snare 2.

The operating unit 102 includes a main body portion 121 which has a thin and elongated cylindrical shape and a slider 122 which is a wire operation handle attached to the main body portion 121 to be slidable in the longitudinal direction of the main body portion 121.

A tubular bending prevention portion 121a is provided at the distal end of the main body portion 121. Further, a ring portion 121b is formed at the proximal end of the main body portion 121 for the user to insert and hook a thumb thereinto. The bending prevention portion 121a is formed by using, for example, the same material as that of the flexible sheath 111. Further, the main body portion 121 other than the bending prevention portion 121a is formed by using, for example, a synthetic resin material such as ABS resin.

The slider 122 is movable forward and backward in the longitudinal direction of the main body portion 121 and includes a pair of ring portions 122a and 122b which are formed at symmetric positions with respect to the center axis of the main body portion 121 and are used for the user to insert two fingers other than a thumb thereinto. A part of the slider 122 protrudes inside a hollow portion of the main body portion 121 and the proximal end portion of the operation wire 3 engages with the protrusion (not illustrated). Accordingly, the operation wire 3 moves and backward in synchronization with the forward and backward movement operation of the slider 122.

When the slider 122 is operated to slide toward the proximal end, the loop portion 21 of the snare 2 is extended linearly and is drawn into the distal end portion of the flexible sheath 111 to be accommodated therein. On the contrary, when the slider 122 is operated to slide toward the distal end so that the snare 2 protrudes from the flexible sheath 111, the snare 2 is deployed (see FIGS. 2 and 3).

Figure 4:
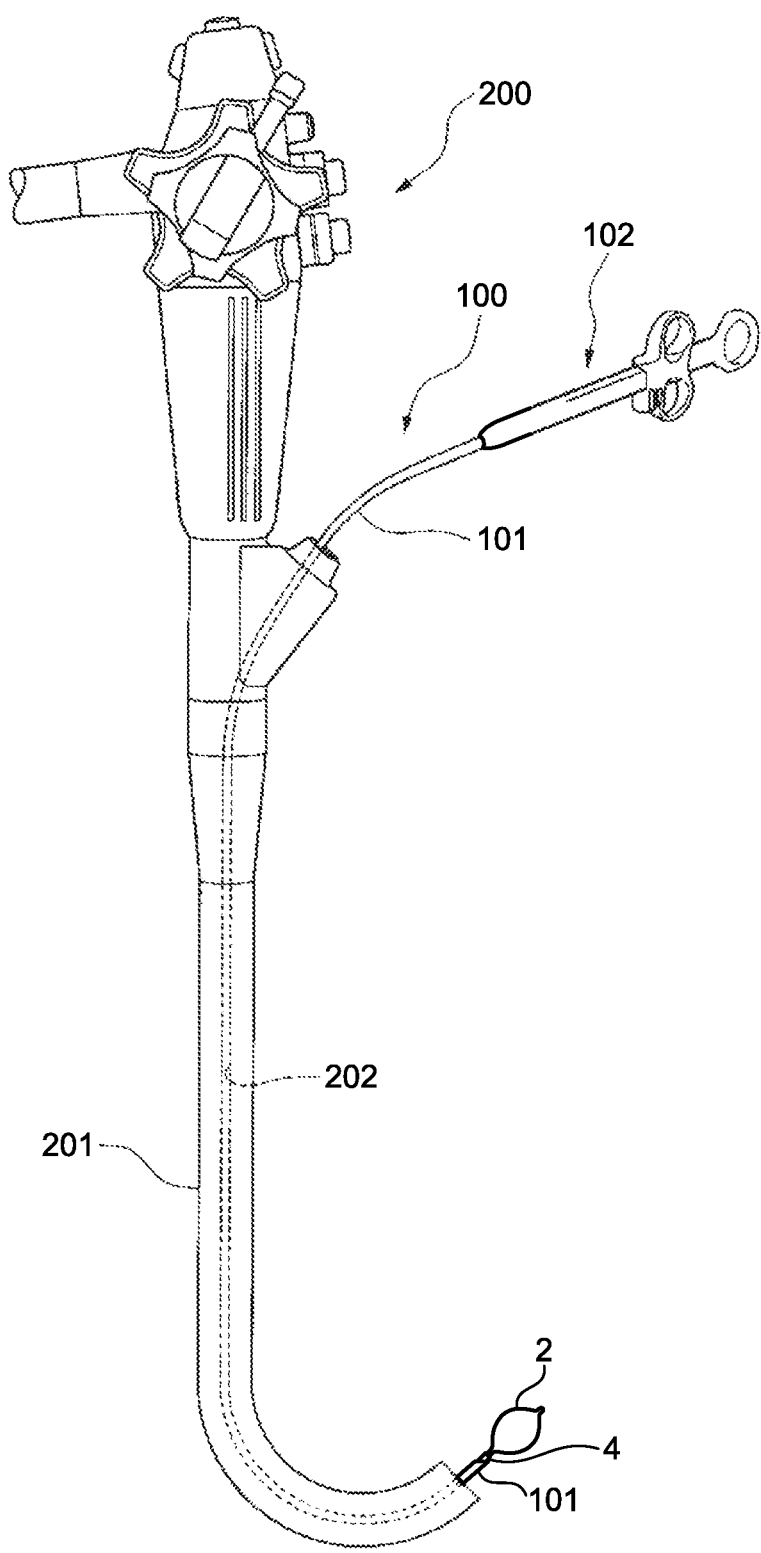
FIG. 4 is a perspective view illustrating a state where the treatment instrument is used.

FIG. 4 is a perspective view illustrating a state in which the treatment instrument 100 with the above-described configuration is used. Specifically, this is a perspective view illustrating a state in which the treatment instrument 100 is used while being inserted into the channel of the treatment instrument of the endoscope. The insertion portion 101 of the treatment instrument 100 is inserted into a channel 202 formed in an insertion portion 201 of an endoscope 200 to be movable forward and backward. FIG. 4 schematically illustrates a state where the snare 2 is deployed from the flexible sheath 111 at the distal end portion of the endoscope 200.

Figure 5:
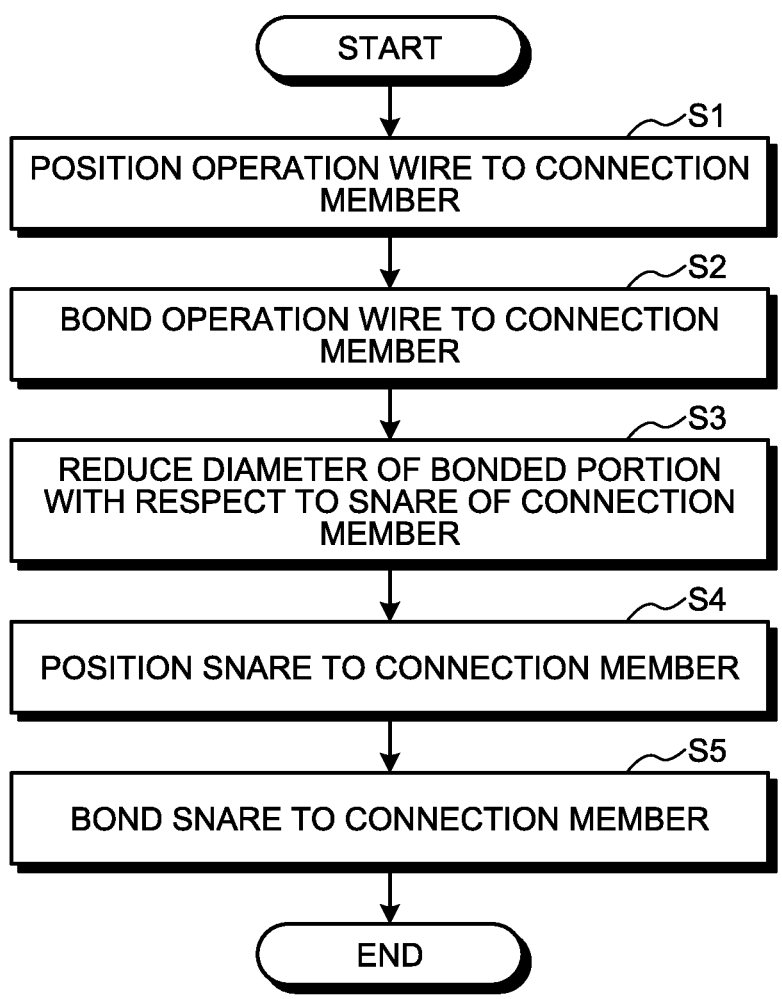
FIG. 5 is a flowchart illustrating an outline of a connection method according to the embodiment.
Figure 6:
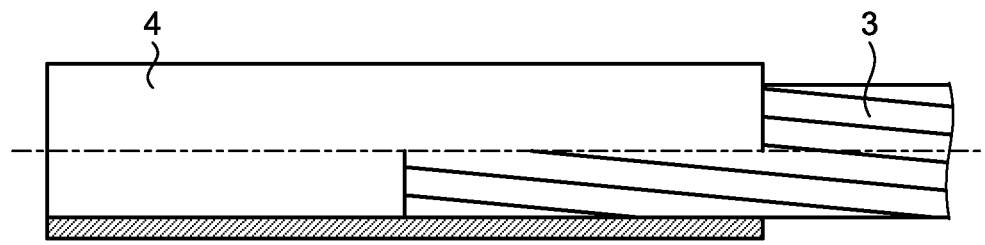
FIG. 6 is a partially cross-sectional view illustrating a state where an operation wire is positioned to a connection member.

Next, a connection method according to the embodiment will be described with reference to a flowchart illustrated in FIG. 5. First, the distal end portion of the operation wire 3 is inserted from the opening portion at one end side into the hollow portion of the connection member 4 to be positioned with respect to the connection member 4 (Step S1). Specifically, the foremost distal end of the operation wire 3 is positioned at the center of the connection member 4 by using a positioning jig. FIG. 6 is a partially cross-sectional view illustrating a state where the operation wire 3 is positioned with respect to the connection member 4.

Figure 7:
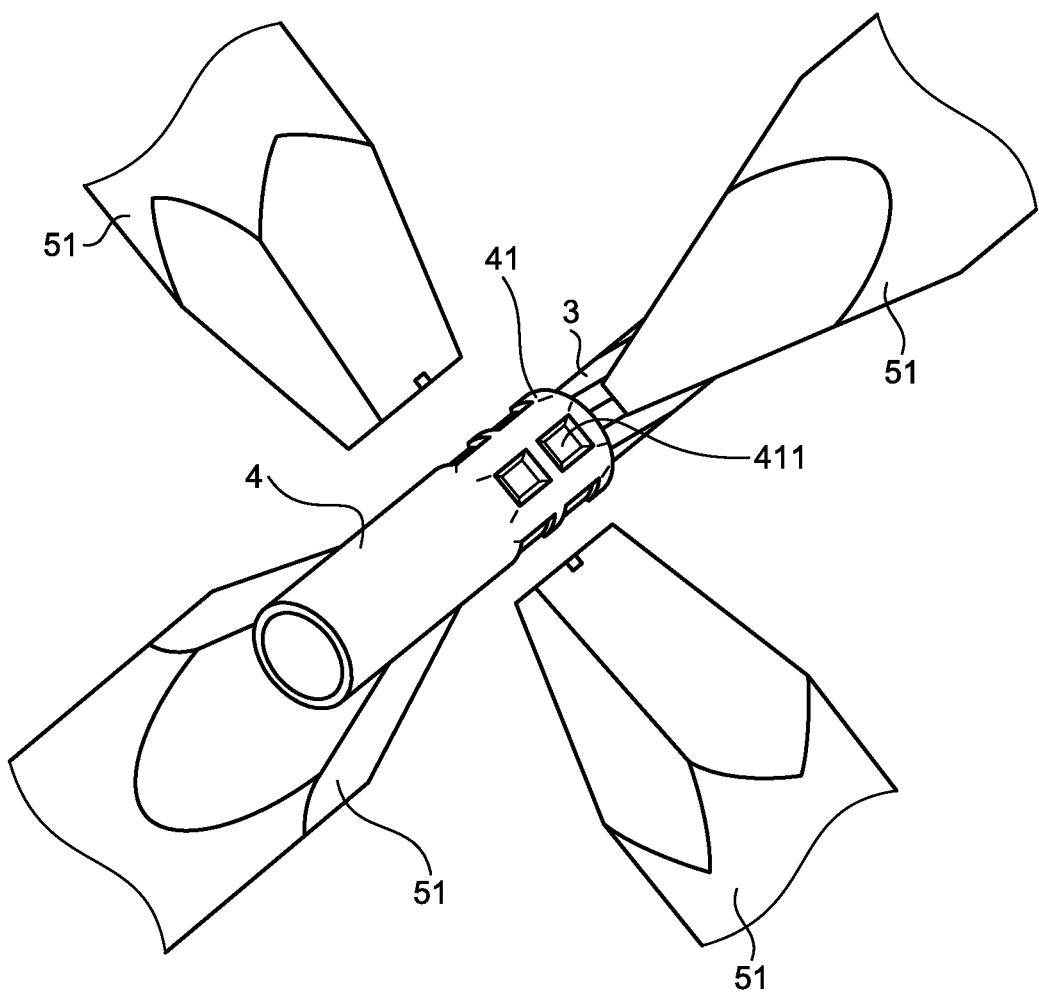
FIG. 7 is a diagram illustrating an outline of a step of bonding the operation wire and the connection member to each other.
Figure 8:
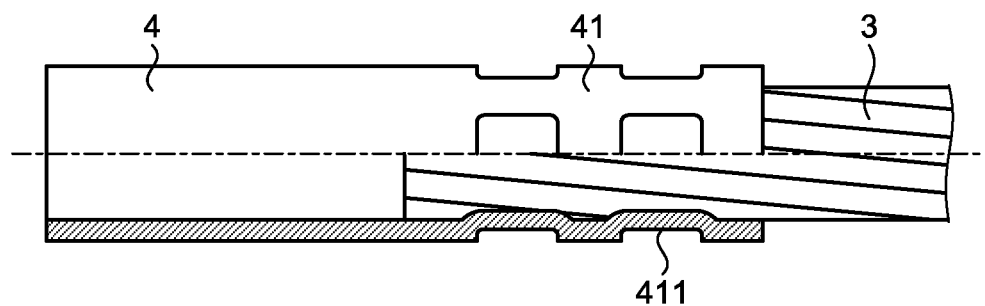
FIG. 8 is a partially cross-sectional view illustrating a state where the operation wire is bonded to the connection member.

Next, the operation wire 3 and the connection member 4 are bonded to each other (Step S2). FIG. 7 is a diagram illustrating an outline of a step of bonding the operation wire 3 and the connection member 4 to each other. As illustrated in FIG. 7, four punches 51 are pressed in synchronization from the outer periphery of the connection member 4 toward the center axis so that a concave portion 411 is formed at the outer wall of the connection member 4 and the operation wire 3 and the connection member 4 are crimped to each other. In this meaning, FIG. 7 illustrates a state where the crimping by four punches 51 ends and four punches 51 are separated from the connection member 4. Accordingly, the wire connection portion 41 is formed. FIG. 8 is a partially cross-sectional view illustrating a state where the operation wire 3 is bonded to the connection member 4. Here, Step S1 and Step S2 constitute a first bonding step.

In the punch 51 used in Step S2, a tip mold portion is provided with two convex portions and a bonding target member is provided with two concave portions 411 in the longitudinal direction. Incidentally, the number (number of rows) of the concave portions in the longitudinal direction formed in Step S2 is not limited to two and may be one or three or more. Further, it is needless to mention that the dimension or shape of the convex portion of the tip mold portion of the punch 51 may be also appropriately changed in response to the condition of the dimension, shape, or required bonding strength of the bonding target member.

An indent crimping device for pressing the four punches 51 against the connection member 4 in synchronization is not limited as long as the device may position the four punches 51 to a predetermined position in synchronization. For example, a crimping tool of a closed barrel terminal for electrical wiring of a general-purpose product may also be diverted.

Figure 9:
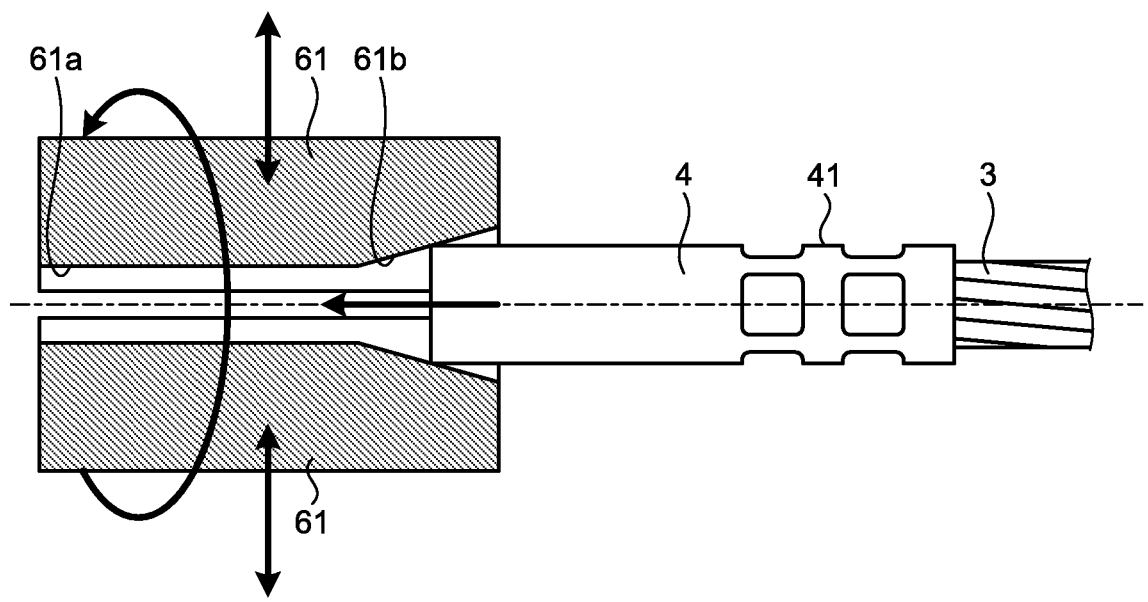
FIG. 9 is a diagram illustrating an outline of swaging processing performed when the connection member is reduced in diameter.
Figure 10:
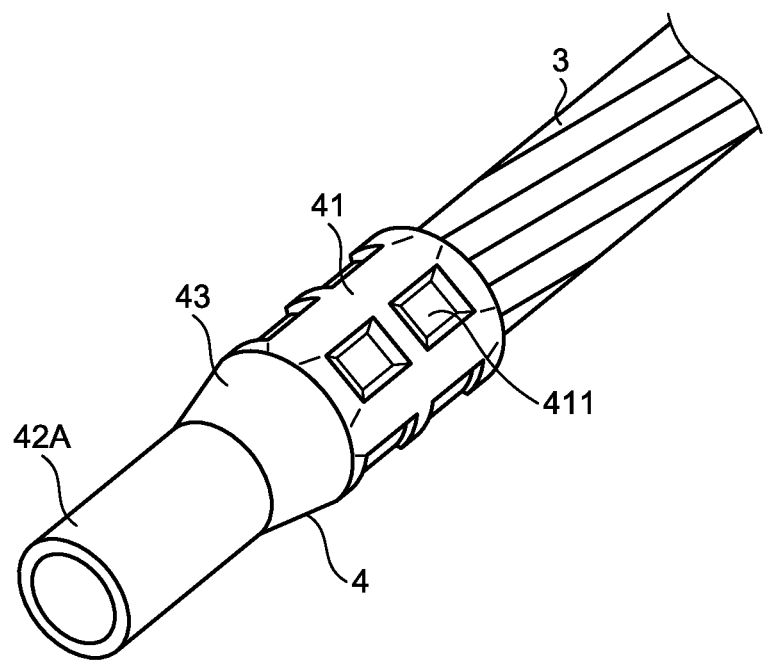
FIG. 10 is a perspective view illustrating a shape of the connection member after diameter reduction processing.
Figure 11:
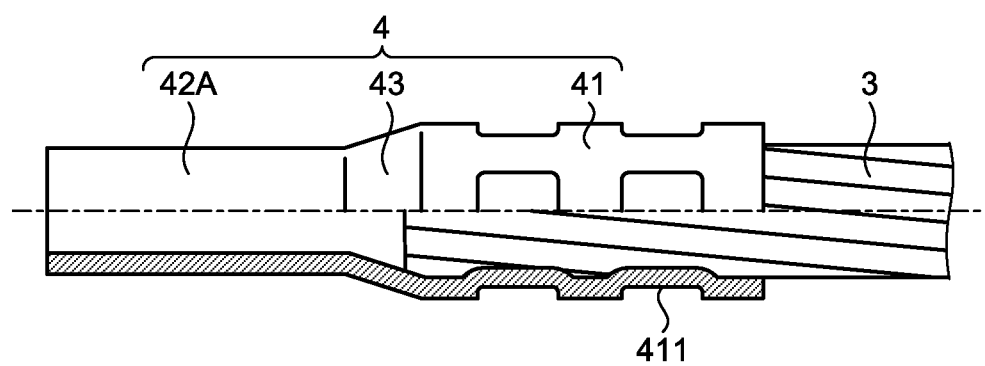
FIG. 11 is a partially cross-sectional view illustrating a shape of the connection member after diameter reduction processing.

Next, a portion bonded to the snare 2 at the other end side of the connection member 4 is reduced in diameter (Step S3). FIG. 9 is a diagram illustrating an outline of swaging processing performed at the time of reducing the diameter of the connection member 4. A swaging mold 61 illustrated in the drawing is provided with a mold portion 61a which substantially has the same diameter as the reduced target diameter and a tapered portion 61b which is smoothly guided with respect to the mold portion 61a at the end portion of the connection member 4 and molds an intermediate portion 43 of the connection member 4. In order to perform diameter reduction processing, the pair of swaging molds 61 is installed to be disposed at symmetrical positions with respect to a rotation axis of a swaging device (not illustrated) and is moved forward and backward in synchronization within a predetermined range in a direction orthogonal to the rotation axis while the pair of swaging molds 61 is rotated about the rotation axis. In this state, the connection member 4 fixed to the distal end of the operation wire 3 is inserted to a predetermined processing position along the axial direction and the insertion portion of the snare 2 is reduced in diameter. Accordingly, as illustrated in FIG. 10 and FIG. 11 which is a partially cross-sectional view of FIG. 10, a reduced distal end portion 42A and the intermediate portion 43 are formed.

Generally, it is not easy to process a micro component such as the connection member 4 because it is difficult to handle the component. On the contrary, in the case of the connection method according to the embodiment, since the operation wire 3 is connected to the connection member 4, it is easy to handle the component by holding the operation wire 3. Further, since an inexpensive general-purpose device is commercially available as the swaging device, it is possible to greatly reduce the cost as compared with a case where the connection member 4 is manufactured by cutting even if the initial investment cost is included.

After Step S3, the proximal end portion 23 of the snare 2 is inserted from the opening portion of the distal end portion 42A into the hollow portion and is positioned to the connection member 4 to be brought into contact with the end surface of the operation wire 3 connected to the connection member 4 (Step S4). At this time, the positioning is performed while maintaining a state where the loop portion 21 and the distal end portion 22 passes through one plane (the attachment surface). Specifically, the positioning is performed so that two wires constituting the proximal end portion 23 are aligned side by side to be located at the same plane as that of the attachment surface or two wires are aligned vertically in a direction orthogonal to the attachment surface. Then, the assembled members are placed on an indent crimping positioning jig (not illustrated).

Figure 12:
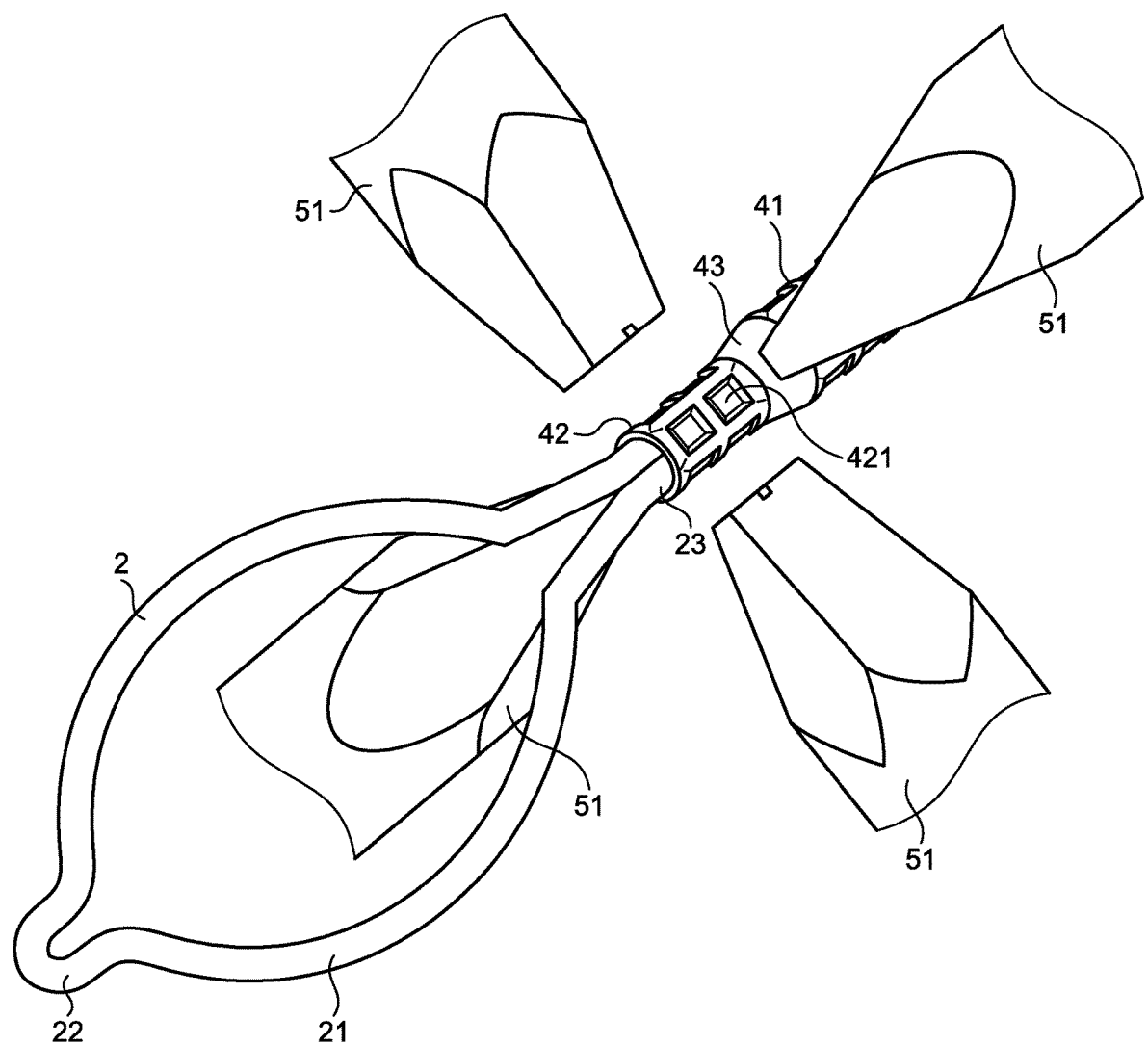
FIG. 12 is a diagram illustrating an outline of a step of bonding the snare and the connection member to each other.

Next, the snare 2 and the connection member 4 are bonded to each other (Step S5). FIG. 12 is a diagram illustrating an outline of a step of bonding the snare 2 and the connection member 4 to each other. As illustrated in FIG. 12, at the time of bonding the snare 2 to the connection member 4, similarly to the case of bonding the operation wire 3 and the connection member 4 to each other, four punches 51 are pressed against the connection member 4 in synchronization so that a concave portion 421 is formed at the outer wall of the connection member 4 and the proximal end portion 23 of the snare 2 and the connection member 4 are bonded to each other by crimping. In this meaning, FIG. 12 illustrates a state where the crimping by four punches 51 ends and four punches 51 are separated from the connection member 4. Here, Step S4 and Step S5 constitute a second bonding step.

Figure 13:
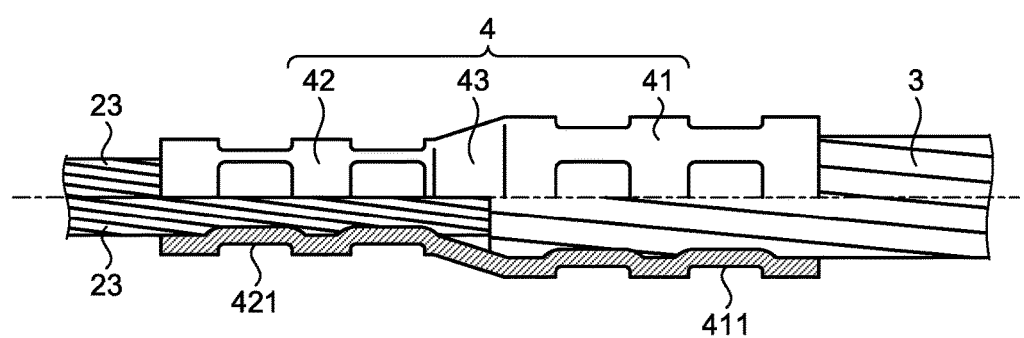
FIG. 13 is a partially cross-sectional view illustrating a state where the snare is bonded.

FIG. 13 is a partially cross-sectional view illustrating a state where the snare 2 is bonded. When an appropriate gap (fitting gap) is formed between the proximal end portion 23 and the connection member 4 in this bonding, the proximal end portion 23 of the snare 2 is bonded to the connection member 4 in an aligned state without causing withering or twisting. Accordingly, the snare connection portion 42 is formed and the connection structure 1 is completed.

According to the above-described embodiment, since the distal end portion of the operation wire 3 is inserted and crimped to a first hole portion opened at one end side of the connection member 4 and the proximal end portion 23 of the snare 2 is inserted and crimped to a second hole portion formed at the other end side of the connection member 4 to have a diameter smaller than that of the first hole portion, it is possible to realize high performance and a reliable contact with the operation wire 3 even when the snare 2 made to have a small diameter is used.

Further, according to this embodiment, since the snare 2 and the connection member 4 are indent-crimped to each other with an appropriate inner diameter dimension (fitting gap), it is possible to stably connect the small diameter snare 2 excellent in resectivity and the operation wire 3 excellent in operability at low cost by using the connection member made of a pipe material which is inexpensive in component cost without causing deterioration of the deployed shape of the snare 2, a large increase in the outer diameter dimension of the bonded portion of the connection member 4, and an increase in the hard bonded portion length of the connection member 4.

Figure 14:
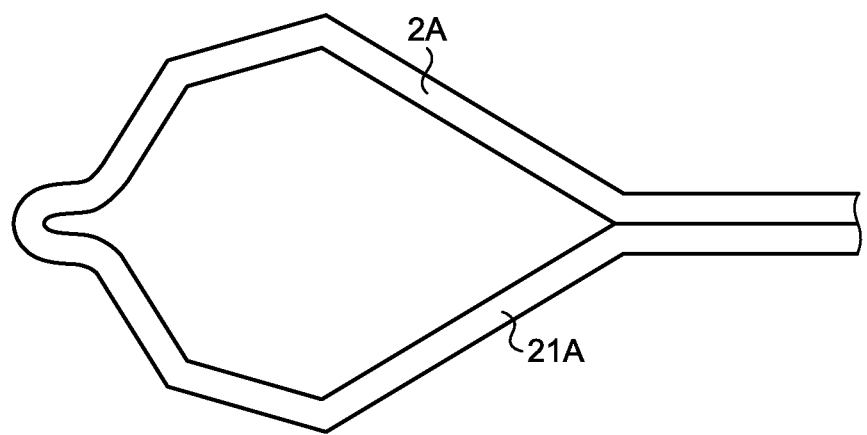
FIG. 14 is a diagram illustrating a shape (a first example) of a snare according to another embodiment.
Figure 15:
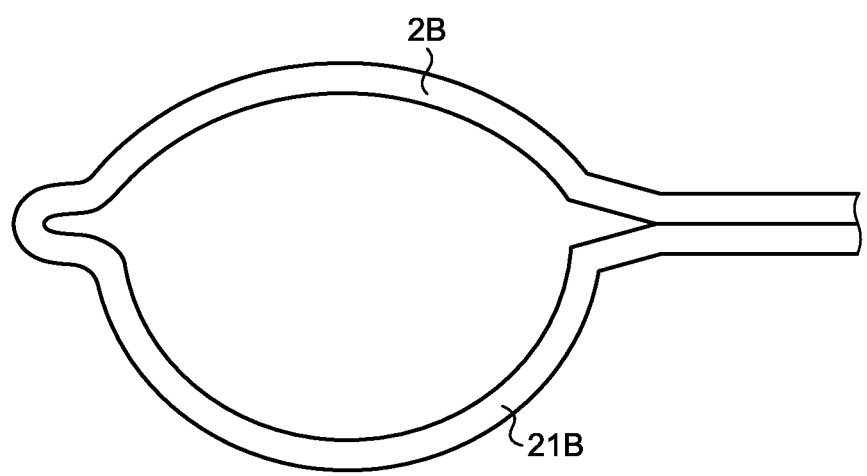
FIG. 15 is a diagram illustrating a shape (a second example) of a snare according to another embodiment.

So far, the mode for carrying out the present disclosure has been described above, but the present disclosure is not limited to the above-described embodiment. For example, the shape of the snare is not limited to the shape illustrated in FIG. 2 and the like. FIG. 14 is a diagram illustrating a configuration of a snare having a different shape. In a snare 2A illustrated in FIG. 14, a loop portion 21A has a substantially polygonal shape. FIG. 15 is a diagram illustrating a configuration of a snare having a different shape. In a snare 2B illustrated in FIG. 15, a loop portion 21B has an asymmetrical shape.

Further, the connection structure according to the embodiment may be also applied to a high-frequency snare (hot snare). In this case, the slider of the treatment instrument includes a terminal which is connected to a high frequency generator and to which the proximal end portion of the operation wire 3 is fixed. Further, the proximal end portion of the operation wire 3 is coated by an insulation coating pipe having an appropriate length. The operating unit or the slider is formed of a synthetic resin material similarly to the above-described treatment instrument 100, but needs to have a sufficient insulation property for the high-frequency current. Incidentally, a configuration necessary for the application of the high-frequency snare is disclosed in, for example, JP 2001-218771 A described above.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing a connection structure, the method comprising:
   inserting a distal end portion of a first wire into a first opening at a first end of a connection member to be crimped;
   reducing a diameter of a hollow portion including a second opening at a second end of the connection member; and
   after reducing the diameter of the hollow portion including the second opening at the second end of the connection member, inserting a proximal end portion of a second wire into the second opening at the second end of the connection member to be crimped, the second wire having a diameter smaller than a diameter of the first wire.

2. The method according to claim 1, wherein:
   the proximal end portion of the second wire that is inserted into the second opening is formed by two ends of the second wire that are bundled, and a portion of the second wire between the two ends forms a snare having a loop shape; and
   the first wire is configured to function as an operation wire operable to pull the snare.

3. The method according to claim 1, wherein a diameter of the proximal end portion is smaller than a diameter of the first wire.

4. The method according to claim 1, wherein reducing the diameter of the hollow portion is performed after the distal end of the first wire is inserted into the first opening.

5. A method of manufacturing a connection structure, the method comprising:
   inserting a distal end portion of a first wire into a first portion of a connection member through a first opening in a first end of the connection member;
   crimping the first portion of the connection member to the distal end portion of the first wire inserted therein;
   after crimping the first portion of the connection member, reducing a diameter of a second portion of the connection member, the second portion having a second opening in a second end of the connection member;
   after reducing the diameter of the second portion of the connection member, inserting a proximal end portion of a second wire into the second portion through a second opening in a second end of the connection member, the second wire having a diameter smaller than a diameter of the first wire; and
   crimping the second portion of the connection member to the proximal end portion of the second wire inserted therein.

6. The method according to claim 5, wherein:
   the proximal end portion of the second wire that is inserted into the second opening is formed by two ends of the second wire that are bundled, and a portion of the second wire between the two ends forms a snare having a loop shape; and
   the first wire is configured to function as an operation wire operable to pull the snare.

7. The method according to claim 5, wherein a diameter of the proximal end portion is smaller than a diameter of the first wire.

* * * * *